US010758106B2

(12) United States Patent
Stojalowski (10) Patent No.: US 10,758,106 B2
(45) Date of Patent: Sep. 1, 2020

(54) REPROCESSING APPARATUS AND A METHOD OF REPROCESSING A LOAD IN A REPROCESSING APPARATUS

(71) Applicant: ASEPTIUM LIMITED, Inverness (GB)

(72) Inventor: Pawel de Sternberg Stojalowski, Munlochy (GB)

(73) Assignee: ASEPTIUM LIMITED, Bishop's Stortford (GB)

(*) Notice: Subject to any disclaimer, the term of this patent is extended or adjusted under 35 U.S.C. 154(b) by 337 days.

(21) Appl. No.: 15/751,871

(22) PCT Filed: Aug. 16, 2016

(86) PCT No.: PCT/PL2016/000088
§ 371 (c)(1),
(2) Date: Feb. 11, 2018

(87) PCT Pub. No.: WO2017/030456
PCT Pub. Date: Feb. 23, 2017

(65) Prior Publication Data
US 2018/0228341 A1    Aug. 16, 2018

(30) Foreign Application Priority Data
Aug. 16, 2015 (GB) .................................. 1514566.7

(51) Int. Cl.
*A61L 2/00* (2006.01)
*A61L 9/00* (2006.01)
(Continued)

(52) U.S. Cl.
CPC .......... *A47L 15/0076* (2013.01); *A61B 90/70* (2016.02); *A61C 19/002* (2013.01);
(Continued)

(58) Field of Classification Search
CPC ............. A61L 2/00; A61L 2/0088; A61L 2/18
(Continued)

(56) References Cited

U.S. PATENT DOCUMENTS

| 6,558,620 B1 | 5/2003 | Sanford | |
| 2007/0193604 A1* | 8/2007 | Weber | A61B 90/70 134/18 |
| 2015/0305818 A1 | 10/2015 | Butrick et al. | |

FOREIGN PATENT DOCUMENTS

| EP | 2362732 | 5/2015 |
| MX | 2015006662 | 8/2015 |

* cited by examiner

*Primary Examiner* — Monzer R Chorbaji
(74) *Attorney, Agent, or Firm* — Andrzej Malarz (57) ABSTRACT

A reprocessing apparatus for washing and cleaning a load comprising a reprocessing chamber, a buffer tank, a buffer tank valve and recirculation valve, fluid distribution devices and plurality of pumps, at least one ultrasonic transducer and a drainage system characterised by said buffer tank is supplied with fresh water and process chemical where buffer tank holds fresh process fluid that is pumped to at least one fluid distribution device and directly into the load, the drainage system for discharging process fluids and recirculation loop for pumping said fluid back the reprocessing chamber, and a method of reprocessing a load in a reprocessing apparatus characterised by that fresh water is mixed with process chemicals externally to said chamber in the buffer tank and delivered to said chamber through fluid distribution devices and internal connecting lines while simultaneously washing the load internally and externally and discharging the fluid from the reprocessing chamber.

9 Claims, 3 Drawing Sheets

(51) Int. Cl.
*B08B 7/00* (2006.01)
*B08B 9/04* (2006.01)
*A47L 15/00* (2006.01)
*B08B 3/04* (2006.01)
*B08B 3/10* (2006.01)
*A61C 19/00* (2006.01)
*B08B 3/12* (2006.01)
*A61B 90/70* (2016.01)
*A61L 2/025* (2006.01)
*A61L 2/18* (2006.01)
*B08B 3/02* (2006.01)

(52) U.S. Cl.
CPC .............. *A61L 2/0082* (2013.01); *A61L 2/025* (2013.01); *A61L 2/18* (2013.01); *B08B 3/02* (2013.01); *B08B 3/045* (2013.01); *B08B 3/102* (2013.01); *B08B 3/12* (2013.01); *A61L 2202/122* (2013.01); *A61L 2202/15* (2013.01); *A61L 2202/17* (2013.01); *A61L 2202/24* (2013.01); *B08B 2203/007* (2013.01); *B08B 2209/005* (2013.01); *B08B 2209/032* (2013.01)

(58) Field of Classification Search
USPC .... 422/28, 32, 509–510, 292, 300; 134/6, 8, 134/56 R
See application file for complete search history.

REPROCESSING APPARATUS AND A METHOD OF REPROCESSING A LOAD IN A REPROCESSING APPARATUS

CROSS-REFERENCE TO RELATED APPLICATIONS

This international patent application no. PCT/PL2016/000088 is entering the United States according to rules 35 U.S.C. 371.

BACKGROUND OF THE INVENTION

Field of Invention

The present invention relates to the decontamination sciences in general, and more particularly to equipment for reprocessing (washing and disinfecting), including washers and washer disinfectors with and without ultrasonic cleaning, surgical instruments and equipment used in healthcare, including medicine and dentistry, and morgues, laboratory and veterinary settings, where the instruments and equipment are contaminated or potentially contaminated with biological or chemical material.

Description of Related Art Including Information Disclosed Under 37 CFR 1.97 and 1.98

Instrument reprocessors (washers and washer disinfectors) are commonly known, such ones presented in patents US 2007/0193604 A1, US2015305818, EP2362732 and MX2015006662 are used to clean surgical instruments and medical equipment that have been exposed to biological or chemical contaminants. Washers typically remove contamination from the surface of instruments and equipment. Washer disinfectors combine washing with disinfection that inactivates (kills) most microorganisms. Sterilisers kill all viable (alive) microorganisms including bacterial spores and viruses. Cleaning, disinfection and sterilisation are essential elements of a typical decontamination cycle for reusable surgical instruments and medical and laboratory equipment.

Cleaning is typically performed by fluids that are applied to contaminated surfaces in the form of sprays, jets, streams, and/or deluges that use mechanical force to clean contamination from surfaces as well as chemical processes that break down contamination to increase cleaning efficacy and speed up the process. When ultrasonic cleaning is used the cleaned content is submerged in a fluid and mechanical energy is released in a process of cavitation that removes contamination from the surfaces in contact with the fluid.

A typical cleaning operation may include a preliminary rinse or ultrasonic cleaning, usually performed manually in a separate piece of equipment, and a pre-wash stage, a wash stage, a rinse stage and/or a final rinse stage, usually performed in a washer or washer-disinfector. In case of washer disinfector operation disinfection is typically achieved by rinsing the load with fluid (usually water) at elevated temperature (60° C. to 100° C.) and/or by exposure of the contaminated content to a disinfecting agent (where the concentration of the disinfecting agent is based on the disinfection dose that contamination must be exposed to). Some washer-disinfectors may include a drying stage at the end of the process. Whenever manual cleaning or pre-cleaning is involved there is a problem with consistency of quality and quality control itself. Manual processes can be effective but that always comes at the cost of efficiency since humans introduce variability to the process that cannot be eliminated and even reduced to a satisfactory level at reasonable cost. Automation of processes is the preferred solutions since it offers consistency of quality at a given known cost. In conventional reprocessors each stage of a washing cycle (prewash, wash, rinse, etc.) typically consists of three basic elements: filling, processing and emptying or discharging.

The reprocessing chamber is filled with the predefined amount of water and if applicable mixed with a predefined amount of one or more chemicals. Water or water and chemical mixture is hereafter known as process fluid. Hot and cold water is typically supplied from the mains supply or dedicated water storage facilities. Rinse water may require pre-treatment to meet the quality standard of the organic and mineral content. During reprocessing process fluid is typically circulated within the reprocessing chamber through the use of one or more pumps that deliver it to the contaminated surfaces of the cleaned load using fluid distribution devices like nozzles or diffusers, and if applicable directly to the inside of hollow instruments through rigid or flexible channels, like in the case of apparatus described in US 2007/0193604 A1. The temperature of the process fluid in the reprocessing chamber may differ significantly at each stage of the process to create optimum cleaning conditions taking into account the chemical used and the specificity off the load. Heating is typically performed within the sump of the reprocessing chamber. At the end of each stage—prewash, main wash, rinse al used process fluid is discharged from the chamber.

In each step of the cleaning cycle during processing, circulating process fluid removes contamination from the surfaces of the cleaned load and then carries the diluted contamination. As it is recirculated within the system diluted contamination gets reintroduced to the load and internal chamber. Therefore if one heavily contaminated instrument carried specific pathogens then those pathogens will be diluted and reintroduced to all cleaned instruments and equipment, including those that were not previously contaminated with this specific pathogen including the insides of other equipment if internal flushing is used. Additionally, contamination consisting that is insoluble or not completely dissolved matter like but not limited to bits of tissue, bones, contaminated wound dressing and coagulated blood or lumped or dried body fluids circulating within the system gets deposited on the load and is delivered to the internal elements of said load. Such contamination may sediment into or get delivered into parts of the load like fine lumens or channels, crevices and small holes or complex mechanisms where it gets trapped. Because of the nature of the conventional reprocessors said contamination may be delivered to parts of surgical instruments that by design do not get directly contaminated during their use on patients. Additionally circulating contamination especially but not limited to long lumen instruments contributes to the biofilm creation that accumulates over time. Even they are consecutively sterilised layers of biofilm build up. Biofilm creates favourable conditions for the further growth of microorganisms, especially inside of instruments and devices where it is more difficult to sterilise, dry after sterilisation and further maintain dry during storage. During reprocessing of complex instruments it is essential to clean the load inside and outside. Conditions for the external and internal cleaning are entirely different and are serviced by different physico-chemical processes—spray cleaning versus flushing. In conventional reprocessors the chemistry that is used in the process is diluted in the whole volume of the reprocessing fluid such that internal and external elements of the load are cleaned with the same process fluid—same chemical and same concentration despite the fact that cleaning conditions are different. The process fluid is exchanged between the following steps of the cycle so the final concentration of contamination within the process fluid drops to what is considered to be an acceptable level, where it can be assumed that the following processes of disinfection and sterilisation will provide the desired level of safety. In theory this approach may be correct but in practise different types and shapes of individual elements of the load present a different cleaning challenge, especially if contamination is introduced to parts of instruments or equipment that are not normally contaminated during use, and it becomes very difficult, if not impossible, to ensure a sufficient level of safety. In a conventional cleaning process, during every stage the entire load is cross contaminated with the sum of all removed contaminants diluted in the fluid. The remaining fluid that has not been discharged, such as, for example, moisture on walls and the load, and fluid trapped in plumbing, is carried over to subsequent stages. The aforementioned types of reprocessors (washer and washer-disinfectors) are typically used in sterile services facilities as well as laboratories, morgues and veterinary practices. In order to further reduce the risk of contamination, especially contamination highly resistant to disinfection and sterilisation procedures, being carried by surgical instruments, medical and laboratory equipment, it is essential to reduce the cross contamination and improve cleaning efficacy of the physical removal of contamination from the overall decontamination process. Increased efficacy also leads to the reduction of the overall process time and cost.

SUMMARY OF THE INVENTION

The present invention relates to reprocessors using non-recirculating, fluid based cleaning and/or washing systems with simultaneous filling, load processing/reprocessing and draining processes with optionally integrated chemical and/or thermal disinfection processes.

The present invention provides a reprocessing apparatus for washing and cleaning a load comprising a reprocessing chamber, a sump located at the bottom of said chamber, at least one buffer tank external to the reprocessing chamber for mixing and holding fresh process fluid, backflow prevention feature to prevent contamination of the water source from said buffer tanks, at least one valve for fresh water supply, fluid lines for delivering fluid from the water supply through and between elements of the apparatus to the drainage system, at least one chemical delivery line for delivering chemical into the buffer tank, instrument baskets/carriers for holding the load, one or more connectors to connect fluid lines into baskets or carriers inside the reprocessing chamber, one or more internal direct connection lines for the load and/or connection lines to direct the fluid into the inside of the load, at least one fluid distribution device and optionally for load without dedicated connecting ports dedicated fluid distribution device for delivering fluid into said load, at least one process pump, at least one irrigation pump, one or more manifolds for distributing the process fluid into the said pumps, at least one heater to heat fluid in the said manifold or pump supply and/or in the sump and/or through chamber walls and/or inside the buffer tank, at least one ultrasonic transducer and a drainage system for discharging the fluids from the reprocessing chamber containing a drain valve and/or a draining pump.

According to a preferred embodiment of the present invention the aforementioned reprocessing apparatus is characterised by that one or more buffer tanks are supplied with cold and/or hot and/or processed and/or purified water through fluid lines from the fresh water source. Said fresh water is delivered into the buffer tank through one or more valves that control said water supply and further through fluid lines and backflow prevention feature like but not limited to an air gap. Buffer tank is also supplied with at least one process chemical through at least one chemical delivery line. Within said buffer tank fresh water and chemicals are mixed and such prepared process fluid is further delivered through fluid lines, buffer tank valve and fluid directing manifold to at least one process pump and at least one irrigation pump.

Process pumps deliver said process fluid through fluid lines to at least one fluid distribution device that distribute said fluid inside the reprocessing chamber such that contamination is washed away from the instruments and internal walls of said chamber. Fluid distribution devices are static or moving and can be further arranged in an array of fluid distribution devices to increase coverage and penetration of the fluid on the load and internal features of the reprocessing chamber. Fluid distribution devices are installed on static or moving channels or arms that are mounted on one or more chamber walls and/or doors and/or lids and/or in the sump and/or on load carriers or baskets.

Irrigation pumps deliver process fluid through fluid lines and if applicable through a non-return valve into the reprocessing chamber and further through connectors further into baskets and/or carriers that hold the load. Said baskets and/or carriers further deliver the process fluid into internal fluid lines and dedicated fluid distribution devices and connection lines that deliver said fluid into difficult to clean elements of the load such like but not limited to internal channels, mechanisms, crevices, narrow gaps, hinges and holes.

Process fluid collects in the bottom of said chamber and the sump where it is drained from by the drainage system containing one or more drain valves or a drain pumps and fluid lines that discharge said fluid from the apparatus. Alternatively when drainage system is disengaged reprocessing chamber gets filled up with such that the load is at least partially submerged in reprocessing fluid for ultrasonic cleaning. Further alternatively while drainage system is deactivated and buffer tank valve is closed cutting fresh fluid supply from the buffer tank process fluid is allowed to recirculate from the sump through recirculation fluid line and recirculation valve through at least one process and/or recirculation pumps back to the reprocessing chamber.

In a preferred embodiment of the present invention there is provided a reprocessing apparatus having a heating element is situated in or adjacent to one or more of the reprocessing chamber walls and/or in the sump heats fluid contained in the reprocessing chamber. Temperature of the fresh reprocessing fluid is elevated with a heater installed inside one or more buffer tanks and/or situated in or around a the manifold distributing fluids into the process and irrigation pumps and/or any fluid line on the supply or discharge side of any process and/or irrigation pump. In accordance with a preferred embodiment of the present invention, there is provided a reprocessing (washing and cleaning) apparatus having a reprocessing chamber, one or more buffer tanks a process and irrigation pumps arranged in a way such that pumps are supplied directly from a buffer tank and deliver the process fluid to the reprocessing chamber. The buffer tank may be supplied from the fresh water supply (hot, cold, and/or pre-treated water) through a backflow prevention mechanism (for example a certified non return valve) or an air gap (designed to water authority specification) that protects the fresh water supply from passing the contamination being processed in the described apparatus back to the mains supply. The buffer tank may be further supplied by process chemistry in liquid and solid form through one or more chemical delivery systems that control the desired quantity of said chemicals in the process fluid.

In a preferred embodiment of the invention the process pump delivers fluid directly through one or more fluid distribution devices that distribute the fluid within the chamber to clean a contaminated load and the internal walls of the reprocessing chamber while irrigation pump delivers the process fluid into the inside of specific elements of the load or to dedicated fluid distribution devices and internal connection lines specific to said element in order to remove contamination from the internal and difficult to access surfaces of the load. The cleaning action may rely more on mechanical action created by the pressure of the fluid, rather than on fluid volume as in conventional washers. Fluid delivery devices may be in the form of at least two nozzles creating flat or conical sprays that are mounted directly or indirectly on moving arms (usually rotating) attached to chamber walls, doors or openings or mounted to carriers, baskets or enclosures that the contaminated load is located in as well as in the form of rigid and flexible channels or delivery lines with connectors or ports that deliver fluid directly into instrumentation.

In some embodiments of the present invention fluid distribution devices may come in the form of one or more static or moving nozzles or diffusers, arrays of nozzles or diffusers installed on static or moving (usually rotating) motorised and non-motorised arms or channels. Dedicated fluid distribution devices may come in the form but not limited to of tubes, vessels, pockets, holes and manifolds with internal nozzles and holes delivering fluid directly to particular elements of the load (instruments and/or equipment). Internal fluid connection lines may come in the form of but not limited to rigid and flexible tubes, hoses, channels and manifolds with or without connectors that are attached directly to the insides of the load. Fluid distribution devices or arms or channels may be installed on can be mounted directly on the walls, top, bottom, doors or sealing lids of the reprocessing chamber, inside the sump or alternatively mounted on load carrier systems, instrument baskets and enclosures, instrument holders and accessories. Fluid distribution devices may also come in the form of vessels and/or capsules specifically designed for particular types of the load or parts or certain elements of the said load. Within said vessels fluid is distributed such that problematic and difficult to clean elements are effectively covered and penetrated by the process fluid. Choice of the type of fluid distribution devices to be used in a particular embodiment will depend on the needs of the specific processes and specific loads.

The at least one process pump and irrigation pump may pump clean fluid from the buffer tank into the chamber, whilst the drainage system discharges fluid from the sump, so that no process fluid is recirculated from the sump to the reprocessing chamber, during a substantial portion of the washing process. For example, this may occur during at least 10%, preferably at least 25%, or in case ultrasonic cleaning is used at least 10% of the washing process. Process pumps and irrigation pumps can but do not have to work simultaneously and neither have to work throughout the entire duration of the process.

Since the process pump obtains fluid from a fresh fluid source rather than from the sump during the washing stage, one or more of the process and irrigation pumps may work independently of the amount of water in the sump, so that the process pump does not require a minimum amount of fluid in the sump.

In accordance with preferred embodiment of the present invention fluid may be delivered directly into equipment or instrumentation being decontaminated in order to perform flush or irrigation cleaning or disinfecting of the internal elements of said equipment or instrumentation. In this case fluid distribution devices may also come in a form of rigid or flexible channels with connectors or docking ports that connect directly and deliver process fluid into the instrumentation and cleaned equipment. Such a procedure may be particularly appropriate for complex, lumen or hollow surgical and veterinary instrumentation. Fluid may be supplied by one or more process pumps (which in some embodiments may be the same as the one delivering fluid into fluid distribution devices or may be independent, depending, for example, on the flush and irrigation pressure required for internal cleaning) through rigid or flexible fluid lines or channels. In some embodiments a fluid line that supplies the instruments directly may be connected though a connection port mounted on a chamber wall, door or lid. In other embodiments of the preferred invention it may be connected indirectly through, for example, the instrument carrier, basket, holder or enclosure that is further connected through a connector in chamber walls, doors or lids to one or more process pumps. Fluid distribution devices aim to maximise the coverage and penetration of the process fluid into and onto the contaminated load to increase the probability of contamination removal from all surfaces that may have been exposed to the source of contamination, including external and internal surfaces of the equipment and instrumentation being processed. Additionally fluid distribution devices may direct the fluid in such manner that not only the load coverage may be maximised but also internal chamber walls may be decontaminated at the same time ensuring the entire environment enclosed within the chamber is sufficiently reprocessed.

Inside the reprocessing chamber removed contaminants together with the used fluid drop down, for example by the force of gravity, and are collected in the sump located at the bottom of the chamber. An independent drainage system may remove used process fluid from the chamber and discharge it directly into the drain simultaneously while load is being washed in the reprocessing chamber. Therefore no cleaning time need be lost for filling of the reprocessing chamber and draining time may be significantly reduced. After leaving the chamber drainage can rely on gravity or be assisted by a drain pump, for example in case the mains drain point is above the lowest point of the drainage system plumbing or in case waste water must be pushed a long distance.

In accordance with another aspect of the present invention, in some embodiments of the invention the washing apparatus has a reprocessing chamber equipped with ultrasonic generator and one or more ultrasonic transducers or ultrasonic transducer arrays or banks that can be mounted outside and/or inside of the reprocessing chamber on walls, doors and other elements of the chamber that get submerged or partially submerged by the cleaning fluid or anywhere on the outside of the chamber walls or doors below the process fluid water line. Ultrasonic transducers generate ultrasonic waves in fluid that cause cavitation in the volume of the fluid and produce shockwaves during cavitation bubble collapse that remove contamination from surfaces in direct contact with the fluid within which cavitation was induced. Cleaning methods including use of ultrasonic energy are hereafter known as ultrasonic cleaning. For ultrasonic cleaning to be effective a load must be submerged in the fluid so that substantially all contaminated surfaces are exposed to it.

The invention provides apparatus for the washing and disinfection of medical, dental, laboratory and veterinary instruments and equipment. The washing aims to physically remove contamination from the surface of processed equipment and instrumentation. Process fluid in the form of fresh water or fresh water solution of cleaning chemistry may be delivered under pressure to the contaminated load to remove contamination from the load's surfaces. Alternatively, for complex instrumentation ultrasonic cleaning may be used in the process.

The preferred embodiment of the present invention having a process pump and/or irrigation pump delivering fluid from a buffer tank to the fluid delivery devices or directly into the load inside the chamber whilst the process fluid is drained from the chamber allows for seamless transition between the subsequent stages of the wash—prewash, main wash and rinsing as there is no need to separately fill and empty the chamber. Filling and draining are not separately existent in the traditional understanding of the art—both processes happen simultaneously while washing. In a conventional washer even up to 30% of processing time can be dedicated to filling and emptying of the chamber and sump but the present invention allows for this time to be saved or used to extend the washing stage, which maximises performance of the described apparatus.

Additionally in a non-recirculation washing setup processed fluid is removed from the chamber and the contamination contained within it is not reintroduced into the load, unlike in conventional washers. This is particularly important in the early stages of the process (prewash) where the amount of contamination is highest. Diluted contamination in conventional washers gets redistributed to areas that are not usually contaminated during use of the instrument (e.g. handles of surgical instruments). This is of particular importance for all hollow and fine lumen instrumentation as well as equipment with internal channels and mechanisms. Such contamination is likely to penetrate into small gaps, holes and crevices where it sediments and is extremely difficult to remove. Within the methods and machines described herein, once removed the contamination is not reintroduced. This is also particularly important during the rinsing stage where the residue of the chemicals need to be washed away. The load is sprayed and its internal elements irrigated with fresh clean process fluid and this stage of the cycle can therefore be shortened in favour of a longer washing stage. Flushing or internal irrigation of cannulated or hollow objects may be performed with fresh process fluid only during the prewash, main wash and rinsing portions of the cycle.

In accordance with another aspect of the present invention, in some embodiments the reprocessing apparatus has a reprocessing chamber, a sump at the bottom of the reprocessing chamber for collecting process fluid, and a fluid line connecting the sump with the supply inlet to one or more process pumps different to the primary process pumps supplied from the buffer tank or alternatively a fluid line containing one or more control valves connecting the sump with the supply inlet to one or more process pumps to provide a recirculation option for specific portions of the washing and disinfecting cycle only. This may be particularly important for the disinfection stage where process fluid becomes the carrier of the disinfecting dose in the form of heat (temperatures above 60° C.) or chemical disinfecting agent. In order to maintain the quality and uniformity of the disinfecting dose within time of disinfection, fluid may be recirculated in the system. It additionally allows conservation of the energy for heating as well as in case of chemical disinfection the amount of the chemical used.

The present invention allows disinfection of the load, which disinfection aims to inactivate (kill) most of the microorganisms remaining after the wash step. It is achieved by exposing the load to a predefined disinfecting dose. The disinfection dose consists of a disinfecting environment within the chamber, which may come in the form of a temperature field above 60° C. (above 80° C. being the preferred temperatures) or the addition of a disinfecting agent, and maintaining that environment for a predefined amount of time. For disinfection to take place a recirculation setup may be engaged where fluid is allowed to be reintroduced to the reprocessing chamber. During this stage the amount of remaining contamination is minimal so engaging recirculation does not carry the same risk of cross contaminating the load as during initial wash. Moreover the circulating fluid delivers the disinfection dose so it can be assumed that circulating medium is disinfected throughout.

In accordance with another aspect of the present invention, there is provided a reprocessing (washing and cleaning) apparatus for medical, dental, laboratory and veterinary instruments and equipment. The washing apparatus has a reprocessing chamber, a sump at the bottom of the reprocessing chamber for collecting process fluid, one or more buffer tanks for holding fresh process fluid, at least one process pump for transferring process fluid from the buffer tank to one or more fluid distribution devices, one or more fluid distribution devices for spraying the process fluid on the contaminated load and internal walls of the reprocessing chamber as well as delivering fluid into the inside of those instruments or equipment requiring internal cleaning, and a heating system for regulating process fluid temperature. In some embodiments of the apparatus at least one heating element is installed in the delivery line to the chamber for regulating the temperature of the incoming process fluid. The heater may be positioned inside and/or outside the line. Additionally in some embodiments at least one heating element is installed on one or more chamber walls—inside or outside—as well as inside or outside the sump of the chamber for regulating chamber wall temperature and process fluid heating especially for ultrasonic cleaning where load gets submerged in fluid and disinfection when recirculating fluid gets gradually heated up.

In accordance with another aspect of the present invention, there is provided a reprocessing (washing and disinfecting) apparatus that includes the use of cleaning, water treatment and disinfecting chemistry. At least one chemical substance is delivered either to one or more buffer tanks where it mixes with fresh water (hot, cold or pre-treated—filtered or processed), depending on the intended use, and at the amount specified by the chemistry manufacturers. As process fluid (mixture or solution of chemicals and water is prepared outside the cleaning chamber it allows to prepare different concentration of chemicals in the process fluid or use different chemicals for internal and external cleaning of the load. This property of proposed invention allows to optimise cleaning conditions for internal and external cleaning separately within the same cycle applied to the same load. Within the current invention cleaning chemistry may be used alongside the mechanical action of sprayed process fluid to improve the efficacy of the cleaning process or directly to the chamber. Concentrations are derived from the volumetric or mass water flow and/or chamber volume. Disinfectants may be added during the disinfecting stage.

Water treatment chemistry is added usually to the final rinse in order to minimise scaling effect and to lower the surface tension of the process fluid to speed up drying.

The invention provides a method for reprocessing a load in a reprocessing apparatus, where said load contains complex non-cannulated and cannulated load including but not limited to medical, dental, laboratory, mortuary or veterinary instruments or equipment said method comprising of the following stages: Delivering fresh water at a temperature below 45° C. through fluid distribution devices that distribute it on the external surfaces of the load as well as internal surfaces of the reprocessing chamber and directly into the complex load though direct connecting line for a predefined amount of time whilst draining the contaminated fluid from the sump through a drainage system. Filling stage comprising deactivating the drainage system and whilst continuing delivering process fluid though the process and irrigation pumps delivering predefined amount of process chemical in the buffer tank to achieve predefined concentration of said chemical in the process fluid for ultrasonic cleaning, allowing the reprocessing chamber to fill up such that load is submerged in the process fluid and simultaneously increasing fluid temperature in the reprocessing chamber to a desired level. Ultrasonic cleaning stage comprising disengaging process pumps, engaging ultrasonic cleaning whilst maintaining desired temperature of the process fluid within the reprocessing chamber and simultaneously delivering predefined amount of process chemical into the buffer tank to achieve desired concentration of process chemistry in the process fluid for internal cleaning where said concentration may be different from one present in the process fluid present the reprocessing chamber, alternatively using different process chemical for internal cleaning and pumping such formulated process fluid from buffer tank into dedicated fluid distribution devices and directly into the load. At the same time removing excess process fluid from the reprocessing chamber. Rinsing stage comprising of engaging the drainage system and process pump and delivering fresh water without chemicals from the buffer tank to the fluid distribution devices and directly to the load through internal connection lines whilst allowing for process fluid containing dissolved contamination and chemical residue to gradually drain out of the chamber. Disinfection stage after load is sufficiently cleaned disinfection stage cleaned within one continuous washing and disinfecting cycle comprising deactivating the drainage system, delivering fresh water, preferably processed or purified and in case of chemical disinfection required amount of disinfecting chemical into the buffer tank and delivering such prepared fresh process fluid into the reprocessing chamber through process and irrigation pumps. Allowing said chamber to fill to a desired level, then simultaneously opening recirculation line through the recirculation valve and disengaging the buffer tank supply by closing the buffer tank valve whilst continuing to recirculate the process fluid continuously from the sump through the process and irrigation pumps back to the reprocessing chamber through fluid distribution devices and one or more direct connecting lines. At the same time gradually elevating process fluid temperature by the inline heater and/or reprocessing chamber wall heater to at least 60° C. (typically over 80° C.) for thermal disinfection or over 30° C. for chemical disinfection and while continually recirculating disinfecting fluid maintaining such created environment for predefined amount of time until all exposed surfaces receive sufficient disinfection dose. Followed by deactivating pumps, heating and activating the drainage system and discharging all remaining process fluid out of the reprocessing chamber. Method may be further followed by draining reprocessing fluid from the reprocessing chamber and optionally drying said load.

According to preferred embodiment of the present invention provided method is characterised by that during filling the reprocessing chamber for ultrasonic cleaning fresh water is mixed with process chemicals externally to said chamber in the buffer tank and delivered to said chamber through fluid distribution devices and direct connecting lines at predefined temperature while simultaneously washing the load internally and externally and washing the internal walls of reprocessing chamber. During ultrasonic cleaning while load is at least partially submerged in the process fluid, preparing fresh process fluid in the buffer tank where said fluid contains the same or at least 5% higher concentration or different type of the process chemical than one present in the reprocessing chamber. Delivering said fresh fluid through at least one irrigation pump periodically with a set duty cycle (10% to 100% based on 10 s to 10 min time intervals) through dedicated fluid distribution device and direct connecting lines into difficult to clean elements of the load. At the same time, removing the excess of process fluid from the reprocessing chamber. Transition between initial rinsing, chemical washing without ultrasonics, reprocessing chamber filling and draining, chemical residue rinsing happens whilst fresh process fluid is continually delivered into the reprocessing chamber through one or more irrigation pumps and/or one or more process pumps.

Method is further characterised by the ability of changing the fluid supply to one or more process and irrigation pumps between fresh process fluid from the buffer tank and used process fluid from the sump while continually washing the load internally and externally by supplying process fluid to the fluid distribution devices and direct connection lines. Additionally while process pumps and irrigation pumps are supplied from buffer tank washing process starts immediately without having a minimum amount of process fluid in the sump and said pumps may continue washing with chemicals or rinsing with fresh hot, cold, processed and/or purified water only while reprocessing fluid is being drained from the reprocessing chamber.

Method is further characterised by process fluid containing one or more process chemical is delivered at a desired temperature to the reprocessing chamber such that undesired foaming caused by too low temperature of the water chemical mixture being pumped by any of the process or irrigation pumps. Additionally fluid is pumped to at least one fluid distribution devices and at least one direct delivery line from buffer tanks while fresh cold, hot, processed and purified water together with one or more process chemicals are introduced into the buffer tanks.

In some embodiments of the proposed invention a method is further characterised by introducing one or more chemicals into the buffer tank or directly into the reprocessing chamber.

The invention provides a method of reprocessing a complex load containing instrumentation with internal channels in a reprocessing apparatus, said method comprising: simultaneously filling the buffer tank with fresh water from the mains water supply though a backflow prevention air gap and mixing said fresh water with one or more cleaning chemicals in the buffer tank creating process fluid that is further pumped from a buffer tank through at least one fluid distribution device that distributes the process fluid on the load and chamber walls whilst pumping said process fluid from the buffer tank into the inside of cleaned devices, such that contamination is washed away from the internal and external surfaces of the load as well as internal surfaces of the reprocessing chamber, whilst simultaneously draining the contaminated process fluid from a sump.

The method may further comprise of inactivating draining of the process fluid from the sump and continue pumping additional fresh process fluid allowing the reprocessing chamber to be filled such that washed load is fully or partially submerged in the process fluid and thereafter delivering energy in the form of ultrasonic waves into the process fluid such that cavitation removes contamination from surfaces submerged in the process fluid while periodically pumping fresh process fluid though (into) the inside of cleaned devices and periodically draining process fluid from the sump such that process fluid level in the reprocessing chamber fluctuates allowing for the simultaneous fluctuation of the standing wave generated by ultrasonics in the submerged part of the reprocessing chamber creating more uniform cleaning conditions in reference to the load in the submerged portion of the reprocessing chamber.

The method may further comprise activating draining of the process fluid from the sump and stopping process chemical dosing into the buffer tank such that process fluid contains fresh water only and pumping said fluid through at least one fluid distribution device into the reprocessing chamber and further pumping said process fluid through (into) the inside of cleaned devices such that remaining contamination and chemical residue from are washed away and drained from the reprocessing chamber.

In accordance with one embodiment of the present invention, there is provided a method of reprocessing (washing and cleaning) of medical, dental, laboratory and veterinary instruments and equipment in a given apparatus with internal irrigation of hollow instruments. The method comprising the steps of:
1. Introducing water from the fresh water source through one or more inlets into one or more buffer tanks;
2. Starting one or more process pumps and irrigation pumps supplied from the buffer tanks, which deliver fresh fluid simultaneously to fluid distribution devices and into direct connection lines connected to instruments or equipment;
3. Washing the contaminated load internally and externally and the chamber internal walls while simultaneously draining used fluid from the reprocessing chamber;
4. Adjusting the fluid temperature though an inline heater or by mixing hot and cold water supply;
5. Introducing a predefined amount of one or more chemicals into the buffer tank through at least one chemical delivery line to achieve a desired concentration in the fluid delivered to the fluid distribution devices;
6. Washing contaminated load internally and externally with the process fluid with a desired concentration of chemicals for a predefined amount of time;
7. Deactivating the chemical delivery system and continuing washing with fresh process fluid containing fresh water only until the chemical residues are washed off the load;
8. Deactivating the process pumps; and
9. Deactivating the draining system once the chamber is emptied of remaining fluids.

In accordance with one embodiment of the present invention, there is provided a method of reprocessing complex loads with complicated internal geometries such like but not limited to hollow channels, mechanisms, crevices, holes, hinges and gaps including ultrasonic cleaning of, but not limited to medical, dental, laboratory and veterinary instruments and equipment in a given apparatus with internal irrigation of hollow instruments. The method comprising the steps of:
1. Introducing water from the fresh water source through one or more inlets into one or more buffer tanks;
2. Starting one or more process and irrigation pumps supplied from the buffer tanks which deliver fresh fluid simultaneously to fluid distribution devices, dedicated fluid distribution devices and direct connection lines connected to instruments or equipment;
3. After a predefined amount of time deactivating draining and allowing for the chamber to fill to a desired level and submerging at least a portion of the load in the process fluid;
4. Simultaneously adjusting the fluid temperature of the washing fluid though the chamber heating system while filling up;
5. Further simultaneously adding a predefined amount of one or more chemicals into the chamber or buffer tanks through a chemical delivery system to achieve a desired concentration while filling up;
6. Deactivating the main process pumps;
7. Engaging ultrasonic cleaning for a predefined amount of time whilst periodically flushing hollow load devices by the irrigation system with fresh process fluid with addition of one or more chemicals (may be different or different concentration to the chemical used for external cleaning) under pressure and controlling fluid level in the chamber by simultaneously periodically draining the process fluid from the reprocessing chamber.
8. Activating draining system to empty the chamber.
9. Starting one or more of the process pumps supplied from the buffer tanks that deliver fresh fluid without any chemicals added simultaneously to fluid distribution devices and irrigation and flushing channels connected to instruments or equipment;
10. Washing contaminated load with the fresh process fluid until the chemical residues are washed off;
11. Deactivating the process pumps; and
12. Deactivating the draining system once the chamber is emptied of remaining fluids.

The invention provides a method of disinfecting a load in said apparatus, said method comprising: recirculating fluid though a recirculation line from the sump of the reprocessing chamber through at least one fluid distribution device that distributes the process fluid on the load and at least one dedicated distribution device and/or internal connecting line that deliver process fluid to the inside of washed load and chamber walls such that a disinfecting environment is created by elevating the process fluid temperature above 60° C. to achieve thermal disinfection or by the addition of a predefined amount of chemical disinfectant to achieve chemical disinfection at lower temperatures, and maintaining this environment for a predefined amount of time until all exposed surfaces receive sufficient disinfection dose.

In accordance with another aspect of the present invention, there is provided a method of thermal disinfecting of but not limited to medical, dental, laboratory and veterinary instruments and equipment in a given apparatus after the cleaning and washing process. The method comprises the steps of:
1. Introducing fresh water through one or more inlet valves into the buffer tank;
2. Starting the process pumps;
3. Filling the chamber to a desired level;

4. Switching from buffer tank supply to recirculation mode;
5. Adjusting fluid temperature though inline heaters or/and chamber heater to reach a desired temperature above 60° C.—typically above 80° C.;
6. Hold the temperature at the desired level for a predefined amount of time or use $A_0$ concept to determine the length of the disinfection stage;
7. Initiating draining system;
8. Deactivating process pump; and
9. Deactivating draining system once chamber is emptied from remaining fluids.

The present invention provides a washer disinfector for medical, dental, laboratory and veterinary instruments and equipment.

An advantage of the present invention is the direct supply of process fluid into the fluid distribution devices and irrigation (internal cleaning system) directly from at least one buffer tank without the need for recirculation.

Another advantage of the present invention may be washing with fresh water and chemical mixture unlike in the case of recirculating washers and washer disinfectors.

Another advantage of the present invention may be washing the inside of hollow and cannulated instruments with fresh process fluid only.

Another advantage of the present invention may be preparation of process fluid chemical solution outside of the reprocessing chamber allowing for different concentration or process chemistry being used for external and internal cleaning.

Another advantage of the present invention may be preparation of process fluid chemical mixture and control its temperature outside of the cleaning chamber allowing for process chemistry to be delivered to the reprocessing chamber at predefined temperature.

Another advantage of the present invention may be the capability to switch between fresh water or chemical mixture washing (with no-recirculation) and recirculation of the process fluid.

Another advantage of the present invention may be the fluid delivery line that prevents backflow and spread of contamination to water supply system.

Another advantage of the present invention may be a significant reduction of cross contamination between different elements of the cleaned load during spraying as diluted contamination is discharged from the reprocessing chamber and does not get reintroduced into the system like in conventional washers.

Another advantage of the present invention may be the seamless transition between stages of the cycle without interruptions for filing and draining.

Another advantage of the present invention may be the gradual temperature adjustment during the cycle that eliminates rapid temperature changes and thermal shock.

Another advantage of the present invention may be the ability for integration of ultrasonication during the cleaning process.

Another advantage of the present invention may be periodical irrigation (internal flushing and cleaning) of the load with fresh process fluid during ultrasonic cleaning.

Another advantage of the present invention is addition of process chemistry into the reprocessing chamber for ultrasonic cleaning though irrigation system such that higher concentration of chemistry is first introduced into the inside of the instruments maximising its efficiency inside of the load before being diluted in the process fluid for ultrasonic cleaning.

Another advantage of the present invention is periodical irrigation (internal flushing and cleaning) subsequently draining the excess process fluid from the chamber creating a fluctuation in the water level in the reprocessing chamber during ultrasonic cleaning allowing for more uniform ultrasonic activity in reference to the load.

A still further advantage of the present invention may be the capability for washing and disinfecting in the same chamber.

A still further advantage of the present invention may be the capability for thermal or chemical disinfection in the same chamber.

A still further advantage of the present invention may be self washing/cleaning and disinfection of the reprocessing chamber internal walls.

A still further advantage of the present invention may be its suitability for pass-though and non-pass-though washer disinfectors.

A still further advantage of the present invention may be electronically controlled washing/cleaning and disinfection process.

Another advantage of the present invention may be the adaptability of the times and temperatures of the process to suit various types of loads.

Another advantage of the present invention may be the elimination of a dormant time of the washer that is used for filling and draining in conventional washers.

A still further advantage of the present invention may be the use of higher pressure cleaning systems (in comparison with conventional washers) that allows for more energy being carried by the cleaning fluid thus increasing the efficacy of cleaning.

These and other advantages will become apparent from the following description of the present invention and its variants taken together with the accompanying drawings and the appended claims.

BRIEF DESCRIPTION OF THE SEVERAL VIEWS OF THE DRAWING(S)

The present invention may take physical form in certain parts and arrangement of parts, preferred embodiments of which will be described in detail in the specification and illustrated in the accompanying drawings which form a part hereof, and wherein.

DETAILED DESCRIPTION OF THE INVENTION

Figure 1:
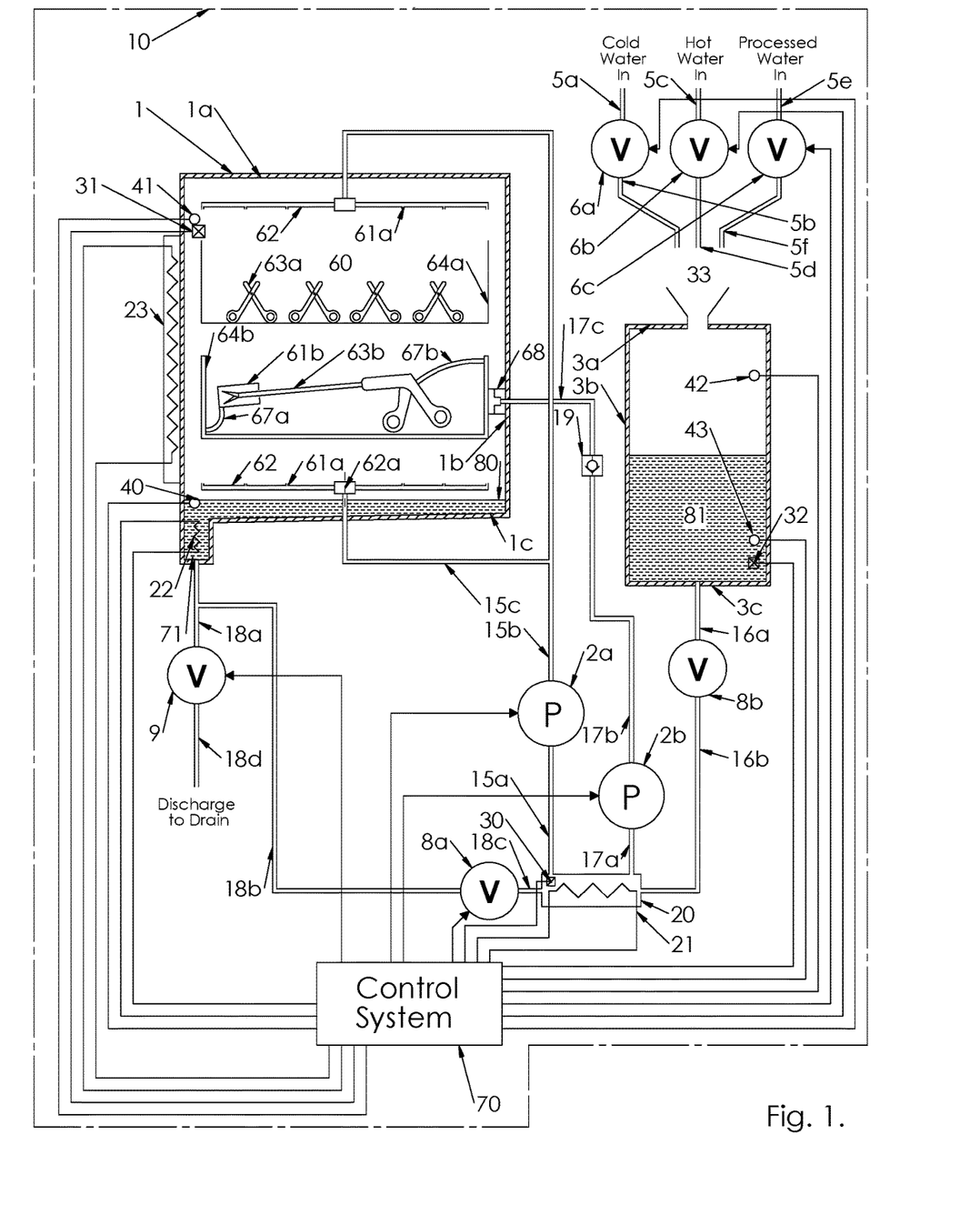
FIG. 1 is a schematic view of an apparatus illustrating the arrangement of the of the present invention allowing for switching between non-recirculation and recirculation reprocessing during the same washing and disinfection cycle.
Figure 2:
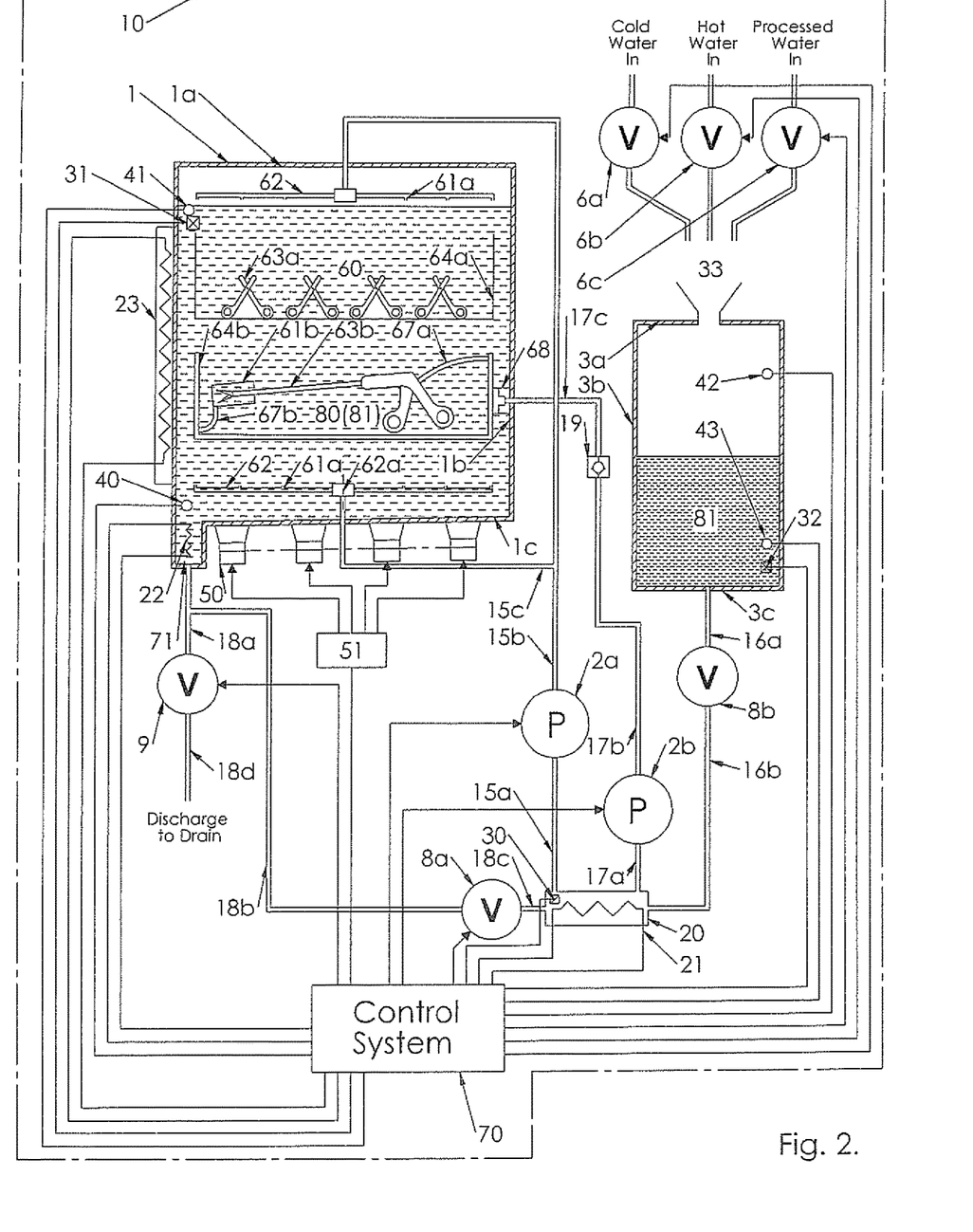
FIG. 2 is a schematic view of a washer illustrating an addition of ultrasonic washing embodiment to the present invention.
Figure 3:
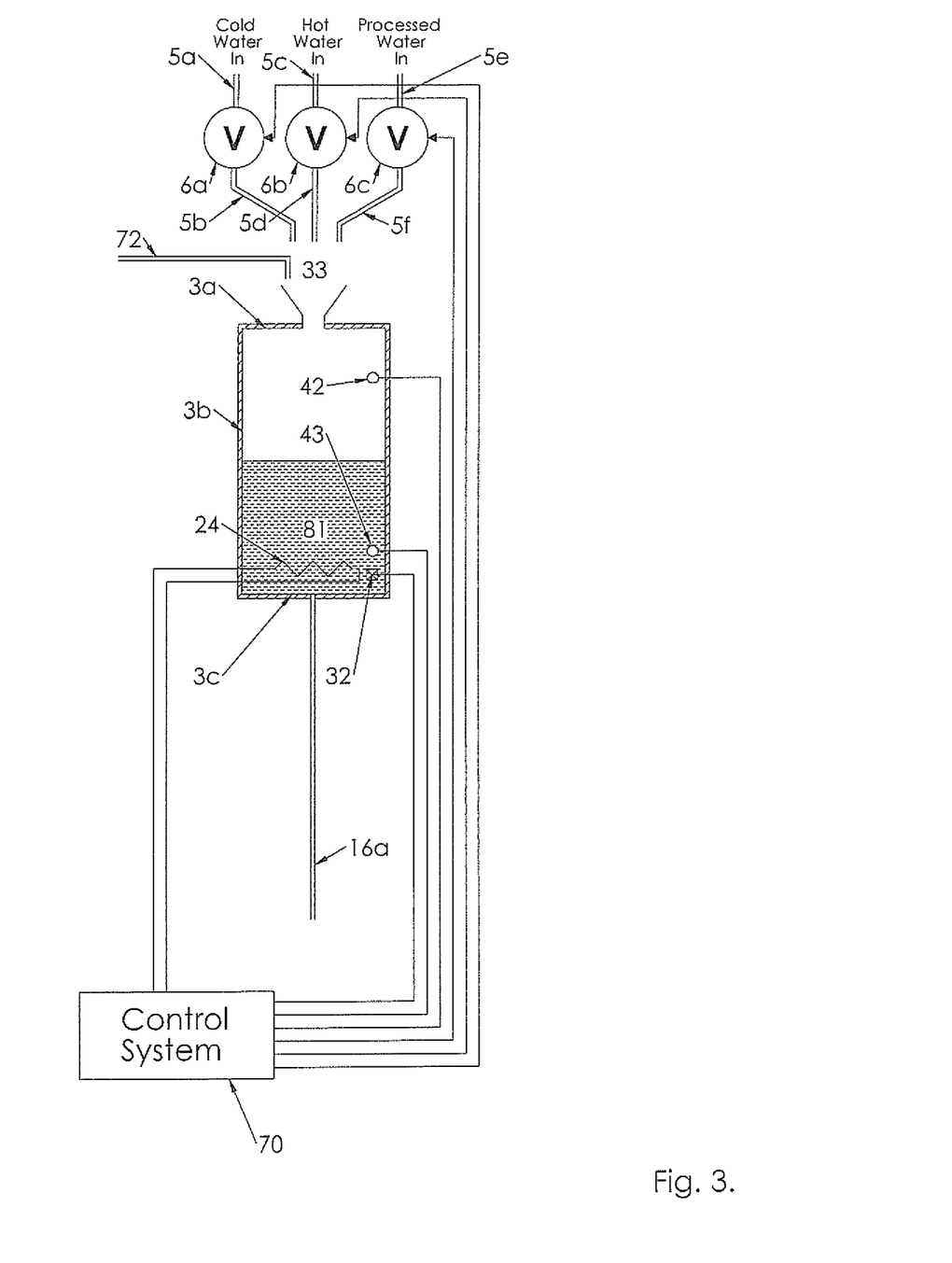
FIG. 3 is a schematic view of a buffer tank with detailed fresh water and chemical supply.

Drawings illustrate preferred embodiments of the invention only, and are not for the purpose of limiting same, FIG. 1, FIG. 2 and FIG. 3. schematically illustrate a medical and laboratory apparatus 10 in different variants—hereafter known as reprocessor—for reprocessing (washing, disinfecting and/or sterilising) of medical and laboratory instruments and equipment 63a and 63b such as, by way of example and not limitation, surgical, medical, dental, veterinary, laboratory and mortuary instruments and equipment—hereafter known as load.

Spray and irrigation washing embodiment as per FIG. 1. is a reprocessor 10 that includes an enclosure 1 that defines a reprocessing chamber 60. Enclosure 1 consists of a top wall 1a and side wall or walls 1b and at the bottom of the enclosure bottom wall or walls 1c sloping towards a sump 71 positioned but not restricted to one side of the enclosure. Alternative arrangement includes a centrally positioned sump with two sloping bottom walls or conical or concave formed sump. One or two side wall or walls 1b and top wall 1a may be used as or consist of doors to the reprocessing chamber 60 used for loading and unloading of the washer 10. Sump 71 is the lowest point in the reprocessing chamber 60 that collects and holds fluids during the reprocessing. Bottom of the sump 71 is shaped to connect to the drain (discharge point) through the drain lines 18a and 18b and a valve 9 that opens to discharge used fluids 80 from the reprocessing chamber 60. Reprocessing chamber 60 is equipped with a fluid 80(81) level control system that consists of at least one level sensor 41—mechanical or electronic. Inside of the reprocessing chamber 60 load 63a and 63b are positioned in containers 64a and 64b, baskets or carriers in accordance with the particular manufacturer's instructions for reprocessing.

Reprocessor 10 also includes a buffer tank 3 having top wall 3a, side wall or walls 3b and a bottom wall 3c. Cold water is supplied from the mains water supply system through valve 6a. Hot water is supplied from the mains water supply system through valve 6b and processed high quality water is supplied through valve 6c. Water from each supply independently passes through the backflow preventing system 33 like an air gap or equivalent before entering the buffer tank 3. Inlet to the buffer tank can be positioned on the top wall 3a, any side wall 3b or inside the buffer tank 3.

Process chemicals (cleaning, disinfecting (sterilising) chemicals or detergents, water conditioning chemistry, etc) are delivered in a liquid form through one or more chemical delivery lines 72 or alternatively said process chemicals are delivered in a solid form as an example but not limited to granules, pallets or tablets and deployed into the buffer tank 3 where it is dissolved to form a liquid. Hot water, cold water, processed high quality water like Deionised or Reverse Osmosis water, mixture of hot and cold water as well as solutions of one or more process chemicals with hot, cold and/or processed water is hereafter known as process fluid 81. Buffer tank 3 holds process fluid 81. Buffer tank 3 includes process fluid 81 level control system that consists of at least one fluid level sensor—mechanical or electronic 43 (optionally together with 42). Buffer tank heating element 24 and manifold heating element allow to preheat process fluid (81) containing process chemicals to the temperatures offering maximum efficiency of operation and reduce the undesired effect of foaming in case some chemical are delivered at too low temperatures. Alternatively process fluid 81 level can be controlled by measurement of the weight, volume of said fluid or by measurement of the mass or volumetric flow of incoming fresh fluids (water and chemicals).

Supply line 16a connects buffer tank 3 through a valve 8b and line 16b with the manifold 20 that is equipped with an inline heater 21 and optionally temperature sensor 30. Manifold 20 though line 15a supplies one or more process pumps 2a that pumps the process fluid 81(80) through lines 15b and 15c into one or more fluid distribution devices 61a that distribute said fluid on the load 63a and 63b as well as internal walls of the enclosure 1. Manifold 20 also supplies process fluid 81(80) through line 17a irrigation pump 2b and line 17b, non-return valve 19, line 17c and connector 68, carrier with manifold 64b and one or more internal lines 67a and/or 67b with dedicated fluid distribution devices 61b into the complex instruments 63b. Fluid distribution devices 61a mounted on arms 62 rotate around the axis 62 by the propulsion force of jets of the process fluid 81(80) coming out of one or more fluid distribution devices (nozzles or diffusers) 61a. Fluid distribution devices 61a are positioned in a way that maximises the coverage of the load 63a(63b) and simultaneously cleans the internal walls of the enclosure 1. Fluid distribution devices 61a or arms/channels 62 they are installed on may be attached to the top 1a, bottom 1c and one or more side walls 1b as well as may be an integral part of the carrier or basket systems 64a and/or 64b that hold the load. Reprocessor 10 is further equipped with a control system 70 that executes the reprocessing program. Control system inputs consist of electrical signals from, but not limited to temperature sensors 30, 31 and 32 and process fluid level control system in the chamber 60 and in the buffer tank 3. Based on the inputs, program parameters and cycle sequence control system 70 activates and deactivates, but not limited to, inlet valves for cold water 6a, hot water 6b, high quality purified water 6c, one or more main pump 2a, irrigation pump 2b, process heating systems 21, 22, 23 and 24 and valves 8a, 8b and 9.

Proposed invention includes interchangeable non-circulation and circulation arrangement for the supply of fluid distribution devices 61a and 61b and internal connection lines 67a, and complex elements of the load 63b that allows to implement disinfecting function to the washer. A recirculation line 18b that connects the bottom of the reprocessing chamber 60 and/or the sump 71 through fluid line 18b, valve 8a and a line 18c to the manifold 20. This connection allows one or more process pumps 2a and one or more irrigation pumps 2b to be supplied from the sump 71 of the reprocessing chamber 60 and recirculate process fluid 80 for specific portion of the reprocessing cycle. Alternatively recirculation may be achieved by installation of a separate at least one process and/or irrigation pump that is supplied directly from the sump 71 and delivers the fluid into fluid distribution devices 61a and 61b and internal connection lines 67a. Variant 1 is illustrated by FIG. 2. showing a schematic view of the reprocessor 10 having enclosure 1 equipped with an ultrasonic cleaning system 51. An embodiment of ultrasonic transducer system is an array of ultrasonic transducers 50 attached, but not restricted to the bottom wall 1c of the enclosure 1. Ultrasonic transducers may be also attached to the side wall or walls 1b. Alternative embodiments of the ultrasonic cleaning system include internally mounted submersible transducers and transducer arrays and banks installed horizontally or vertically inside of the chamber 60. Ultrasonic transducers are powered by one or more ultrasonic generators 50 controlled by the control system 70. Enclosure 1 is further equipped with a heating system that consists of one or more surface heaters 23 attached to at least one side wall 1b or bottom 1c and/or at least one sump heater 22. In order to control the quantity of process fluid inside of the chamber 60 one or more fluid level sensors 40 (mechanical or electronic) indicate the fluid level in the chamber 60. Additionally valve 8b may prevent the backflow of process fluid from the reprocessing chamber 60 to the buffer tank 3 in the specific portions of the cycle.

Proposed invention includes independent temperature control and adjustment variant in the buffer tank 3 that is illustrated by FIG. 3. Figure shows a schematic of the buffer tank 3 having a temperature sensor 32 and a heater 24 inside the buffer tank 3. Alternatively temperature of fluid 81 in the buffer tank 3 can be regulated by a heater mounted on (inside and outside) any side walls 3b or bottom 3c of the buffer tank 3. Heater 24 and temperature sensor are positioned below the water level 43.

Referring to the basic operation of the reprocessor 10. Water from the mains cold, hot supply or purified water source enters the buffer tank 3 through delivery lines 5a, 5c and 5e, valves 6a, 6b and/or 6c and delivery lines 5b,5d,5f and backflow preventing air gap 33 or equivalent device. Buffer tank 3 water level control system ensures the process pump 2a and irrigation pump 2b are supplied without interruptions with sufficient amount of process fluid 81 ensuring consistent output flow. Buffer tank 3 also allows to mix cold, hot and purified water with various chemicals a reprocessing cycle may require. Temperature of the process fluid 81 is adjusted by proportionally mixing hot and cold mains water and/or using internal heater 24 that may be installed in the buffer tank 3, process inline heater 21 that installed in the manifold 20. In case of ultrasonic variant of the reprocessor 10 as per FIG. 2. Process fluid 81 and 80 temperature may be further adjusted by a heating system 23 installed on one or more walls 1a,1b or 1c of the enclosure 1. One or more main process pumps 2a delivers the process fluid 81 into the reprocessing chamber 60 through one or more fluid distribution devices 61a that distribute said fluid on the reprocesses load 63a(63b) and removes contamination from its surfaces while simultaneously removing contamination from internal walls 1a, 1b and 1c of the reprocessing chamber 60. One or more irrigation pumps 2b pump the process fluid into the load 63b through dedicated fluid distribution devices 61b and internal connection lines 67a requiring internal reprocessing where contamination is flushed away from the internal surfaces of said load. Said load 63b contains by example but not limitation cannulated, laparoscopic, surgical and laboratory robotic and semi-automated instruments are inserted in whole or in part. Said fluid distribution devices 61b deliver the process fluid onto and into specific parts of said load 63b to more effectively remove contamination from its surfaces. Number and configuration of fluid distribution devices 61a, 61b, internal delivery lines 67a as well as arms 62 depends on the type of load 63a(63b), configuration of the carrier 64a and 64b, type of cleaning process (with and without ultrasonic cleaning), size of the washer 10 and its volume, shape of the reprocessing chamber 60 and cleaning program design.

Inside of the reprocessing chamber 60 moving arms 62 improve coverage of 61a jets and/or streams of process fluid 81 ejected through fluid distribution devices 61a towards the load 63a (63b) that remove contamination from all surfaces exposed to the process fluid 81. Cleaning of hollow load 63b may require additional equipment like individual connection lines 67a for direct connection to the load 63b or dedicated fluid distribution devices 61b connected through lines 67b supplied by the process pump 2b with fresh process fluid 81 though connections on any of the side walls 1b, top 1a and bottom 1c of the enclosure 1 or indirectly though connections 68 to the load carrier system 64b. Used process fluid 80 drops towards the bottom of the reprocessing chamber 60, is collected by the sump 71 and continually discharged from the reprocessing chamber 60 through the drain line 18a, drain valve 9, and further from the washer 10 through lower drain line 18d.

Process is not divided into separate stages in the same way as in conventional reprocessors where washing cycle is typically divided into pre-wash, main wash with chemicals, rinsing or neutralising and if applicable thermal rinse. In conventional washers process fluid recirculates during every stage and is exchanged between them. Present invention continually exchanges process fluid so load 63a and 63b are not sprayed or rinsed and load 63b is not irrigated with used process fluid 80 during at least a portion of the cycle. Processes of filling, reprocessing and draining happen simultaneously. Heating systems adjusts process fluid 81 (80) temperature to the optimum level for a given chemical to maximise overall reprocessing efficiency. Transition between different stages of the cycle like initial rinse below 45° C. and higher temperature wash or between wash with chemicals and rinsing or neutralising rinse happen seamlessly without the need for emptying and refilling the reprocessing chamber 60.

Duration of each stage of the cycle, temperature levels, amount and type of process chemistry used are managed by the controller 70 and may be significantly different for different types of load 63a (63b), process chemistry and but not limited to the overall decontamination process (preceding and following processes). Similarly inclusion of ultrasonic cleaning and/or thermal disinfection in the washing cycle depend on the type of load, used chemistry and but not limited to the overall decontamination process.

With regards to ultrasonic cleaning in the present invention the main process pump 2a and irrigation pump 2b deliver process fluid into the chamber while drain valve 9 is closed to allow the process fluid 81(80) to fill the reprocessing chamber 60 to a predefined level indicated by level sensor 41. Sump heating system 22 and/or chamber wall cleaning system 23 further adjust and maintain process fluid 81/80 temperature within the reprocessing chamber 60. Once desired level like by the way of example but not limitation level 41 is reached main process pump 2a is deactivated and ultrasonic generator 51 is activated that delivers ultrasonic energy into the process fluid 81 in the reprocessing chamber 60 by at least one ultrasonic transducers 50. Ultrasonic cleaning removes contamination from all surfaces of the load 63a and 63b that are in contact with the process fluid 81(80). Removed contamination gets diluted in the process fluid 81 and/or may dissolve in process fluid 81 turning it into a used process fluid 80. During ultrasonic cleaning one or more irrigation pumps 2b may pump the fresh process fluid 81 into the load 63b through internal connecting lines 67a and fluid distribution devices 61b to flush away contamination. Said irrigation pump 2b may operate continually throughout the ultrasonic cleaning stage or periodically based on specific duty cycles. Fluid level in the reprocessing chamber 60 is controlled by periodical opening of the valve 9 and/or engaging drain pump and draining portions of the process fluid 80 at the time. Fluctuating process fluid 81(80) level in the chamber 60 helps making the ultrasonic activity more uniform within the process fluid 81(80) volume. Once contamination is removed from the load 63a and 63b ultrasonic system 51 is deactivated and drainage system is activated to remove used process fluid 80 from the reprocessing chamber 60. Buffer tank is supplied with fresh water and main process and irrigation pumps are activated. Clean process fluid 81 is delivered to the reprocessing chamber 60 to rinse away remaining contamination from the load 63a, internal surfaces of the load 63b and internal walls 1a, 1b, 1c of the reprocessing chamber enclosure 60.

With regards to the inclusion of the thermal disinfection in the present invention, thermal disinfection is used after the washing process when the load is considered clean therefore the amount of residual contamination that may be diluted in the process fluid is minimal.

Because of the need for elevating the process fluid 81 temperature to the level as high as 99° C. it would be impractical to use the same internal arrangement of the reprocessor as during the wash cycle due to high energy use. Referring to the FIG. 1 thermal disinfection involves opening the valve 8a (FIG. 1.) that connect the sump 71 through the drain line 18a, 18b valve 8a and line 18c to the manifold 20 that further allows for one or more process pumps 2a and irrigation pumps 2b to pump the fluid back to the reprocessing chamber 60 through lines 15b and 15c and fluid distribution devices 61a as well as through line 17b, non-return valve 19 and line 17c and fluid distribution devices 61b and the load 63b. Process fluid 81(80) is therefore allowed to recirculate in the system while being heated up by either or all heaters 23, 22 and 21 to a temperature above 60° C. and typically above 80° C. and held at that temperature to achieve a desired disinfection dose within reprocessing chamber 60. 61 are processing chamber 61 are processing chamber.

EXAMPLES

Example of a Washing Process for Moderately Complex Loads Such Like Short Lumen Devices Using Reprocessor 10 in Variant 1

Process Profile:
  Initial rinse 3 min at 25° C.
  Wash with Chemical 5 min at 40° C.
  Rinsing with Purified water 2 min at without heating.

Buffer tank 3 is filled with mixture of hot and cold water. Controller continually adjusts the hot and cold ratio based on the feedback from temperature sensor 32 to get process fluid 81 temperature close to 25° C. Once the minimum water level is reached controller 70 activates main process pump 2a and irrigation pump 2b and starts reprocessing the load 63a and 63b in the chamber 60. Based on the feedback from the temperature sensor 31 inline heater 21 adjusts the temperature of the process fluid 81 to 25° C. inside of the reprocessing chamber 60. After 3 minutes temperature in the buffer tank 3 is readjusted to 40° C. Once temperature sensor 32 reaches the target temperature chemical is added to the buffer tank 3 at a concentration ratio corresponding with the main process pump 2a and 2b output. Simultaneously temperature in the chamber is adjusted to 40° C. based on the feedback from the temperature sensor 31. Once temperature is reached in the reprocessing chamber 60 reprocessing is performed for the duration of 5 minutes. Predefined period of time before the end of the said 5 minutes duration period controller stops the supply of hot and cold mains water and allows the buffer tank 3 to use the remaining water. At the end of 5 min wash controller 70 allows the buffer tank 3 to be filled with purified water and 2 minutes rinsing process starts. After 2 minutes main process pump 2a and 2b are deactivated, reprocessing chamber 60 is allowed to drain and process ends.

Note: Main process pump runs with minimum interruptions from the beginning to the end of the process. Conditions in the chamber are adjusted gradually what minimises the thermal shock to the load 63a and 63b.

Example of a Washing and Disinfecting Process of Highly Complex Loads Such Like But Not Limited to Long and Fine Lumen Devices, Robotic Instrumentation Etc. Using Reprocessor 10 in Variants 2

Process Profile:
  Initial rinse 2 min at below 45° C.
  Ultrasonic Wash with Chemical 10 min at 45° C.
  Rinsing 2 min.
  Thermal disinfection 1 min at 92° C.

Buffer tank 3 is filled with mixture of hot and cold water. Once the minimum water level is reached controller 70 activates main process pump 2a and irrigation pump 2b and start pumping the process fluid 81 into the chamber 60. Within the first 2 minutes controller continually increases the hot and cold water ratio based on the feedback from temperature sensor 32 and gradually gets process fluid 81 temperature from 25° C. to 45° C. Controller 70 gradually increases the initial rinse temperature in the reprocessing chamber 60 to reach 45° C. by increasing the temperature in the buffer tank and adjusting the temperature of the process fluid 81 with the inline heater 21. At the end of 2 minute period drain valve 9 is closed and reprocessing chamber gradually fills up with the process fluid 81 at the temperature of 45° C. Because the process fluid 81 enters the chamber thought fluid distribution devices load is being simultaneously cleaned. Once fluid level 41 is reached controller deactivates main process pump 2a allowing the irrigation pump 2b to pump the fluid from the buffer tank 3 for 15 s during every minute during the 10 minute period while adjusting the concentration of the process chemical to maximise its efficacy for internal cleaning. During ultrasonic cleaning valve 9 is opens for 20 s every two minutes to remove excess process fluid from the reprocessing chamber. Controller activates ultrasonic system 51 and based on the feedback from the temperature sensor 31 adjusts the temperature in the reprocessing chamber with the side wall heater 23 and/or sump heater 22. After 10 minutes of ultrasonic cleaning controller deactivates the ultrasonic generator 51, side wall heater 23 and/or sump heater 22 and opens the drain valve 9 to allow for the used process fluid 80 to discharge from the chamber. That is followed by valve 9 being opened and process fluid 80 drained from the chamber 60. Main process pump 2a and irrigation 2b are activated, buffer tank is supplied from hot water supply only and the inline heater 21 elevates the temperature not exceeding set disinfection temperature while rinsing the load 63a and 63b and removing remaining contamination and chemical residues. After 2 minutes hot water valve is closed until process fluid level 43 is reached in the buffer tank 3. At this point purified water valve 6c opens and drain valve 9 closes to allow purified water to fill the sump 71. Once water level 40 is reached in the reprocessing chamber 60 purified water inlet valve 6c closes, valve 8a opens and valve 8b closes engaging the recirculation system. While process 2a and irrigation 2b pumps recirculate the process fluid 81 temperature is elevated by the side wall heater 23 and/or sump heater 22 until it reaches 92° C. Temperature is then held at that level for one minute delivering desired disinfection dose to the load 63a and 63b. After disinfection stage is finished main process pump 2a and irrigation pump 2b together with heaters 23 and 22 are deactivated, drain valve 9 is opened to allow the chamber 60 and sump 71 to drain. Controller closes valve 8b and process ends.

Note: Main process pump runs with minimum interruptions from the beginning to the end of the process. Conditions in the chamber are adjusted gradually what minimises the thermal shock.

The foregoing description refers to several variants of the present invention. It should be appreciated that described variants are for the purpose of illustration only, and do not limit the scope of protection of the present invention since numerous combinations, alterations and modifications may be practiced by those skilled in the art without departing from the spirit and scope of the invention. It is intended that all such modifications and alterations be included insofar as they come within the scope of the invention as claimed or the equivalents thereof.

The invention claimed is:

1. A reprocessing apparatus for washing and cleaning a load comprising
- a reprocessing chamber (1), one or more instrument baskets/carriers (64a, 64b),
- a sump (71) located at the bottom of said chamber,
- at least one buffer tank (3),
- fluid lines (5a, 5b, 5c)
- connect the buffer tank (3) to water supply through at least one valve (6 a) and/or valve (6 b) and/or valve (6c),
- fluid lines (5d, 5e, 5f) and backflow prevention feature (33),
- at least one chemical delivery line (72) for delivering chemistry to buffer tank (3), fluid lines (16a, 16b) connecting buffer tank (3) through a valve (8 b) with one or more manifolds (20),
- fluid lines (15a, 17a) connect the manifold (20) with at least one process pump (2a) and at least one irrigation pump (2b),
- fluid lines (15b, 15c, 17b, 17c) and if there is a risk of a backflow from the reprocessing chamber (1) to buffer tank (3) valve (19) connect said pumps with at least one fluid distribution device (61a), one ore more connectors (68), optionally one or more internal connection lines (67a), and a dedicated fluid distribution device (61b) with internal connection lines (67b) located in the reprocessing chamber (1),
- said apparatus further comprising
- at least one heater (21) and/or heater (22) and/or heater (23) and/or heater (24),
- at least one ultrasonic transducer (50),
- a drainage system containing a fluid line (18 a),
- a vale (9) and/or a draining pump
- and a recirculation loop connecting sump (71) through fluid lines (18b, 18c) and a valve (8a) with the manifold (20)
- wherein
- the buffer tank (3) is connected to fresh cold and/or hot and/or processed and/or purified water supply through fluid lines (5a, 5c, 5e) and one or more valves (6a, 6b, 6c) that control said water supply and further
- through fluid lines (5b, 5d, 5f) such that the backflow prevention feature (33) represented by but not limited to an air gap prevents fluid from the buffer tank (3) contaminating the water source and said buffer tank
- is also connected to at least one chemical delivery line (72),
- said buffer tank is further connected through fluid line (16a), a valve (8b), fluid line (16b), the manifold (20) to at least one process pump (2a) through fluid line (15a) and further through fluid lines (15b) and (15c) to at least one fluid distribution device (61 a) and
- at least one irrigation pump (2b) through fluid line (17a) and further fluid lines (17b), optionally to prevent a backflow through valve (19) and further fluid line (17c), a connector (68), a basket or a carrier (64 b) at least
- one connection line (67b) and the dedicated fluid distribution device (61b) and/or at least one connection line (67a) to a load (63b), the sump (71) with the drainage system for discharging process fluids (81, 80) from the
- reprocessing chamber (1) through said sump connected to the drain valve (9) or drain pump through fluid line (18a) and further to a discharge point or
- through a recirculation loop comprising of the fluid line (18b) valve (8a) and fluid line (18c) back to the manifold (20) from where it is pumped back in to the reprocessing chamber (1) through at least one process (2a) and/or the irrigation pump (2 b) wherein,
- the reprocessing chamber (1) is further equipped with at least one ultrasonic transducer (50) mounted on the outside walls and/or inside of the reprocessing chamber (1) for ultrasonic cleaning,
- said apparatus being arranged such that it creates at least two parallel and independent fluids paths to deliver the fresh process fluid (81) from the manifold (20) to the reprocessing chamber (1), one delivers said fluid through
- the main process pump (2a) and fluid distribution devices (61a) distributing the fluid on outside surfaces of the load (63a, 63b) and another through the irrigation pump (2b) and dedicated fluid distribution devices (61b) and internal connection lines (67a, 67b) deliver the fluid into the complex load (63b) containing internal channels narrower than 10 mm in diameter, joints, mechanisms, crevices, gaps narrower than 1 mm, hinges and
- holes with depth greater than their diameters, said apparatus further creates two paths for the used process fluid (80), one from the sump (71), to the drainage system and through valve (9) out of the apparatus while the other
- being the recirculation loop back to the manifold (20) through valve (8 a).

2. The reprocessing apparatus according to claim 1 wherein the fluid distribution device 61a may be static or moving and may be arranged in an array of fluid distribution devices (61a) and/or is installed on static or
- moving channels or arms (62) mounted on one or more chamber walls (1a, 1b, 1c) and/or doors and/or lids and/or in the sump (71) and/or on the load carrier or instrument basket (64a, 64b).

3. The reprocessing apparatus according to claim 1 wherein the heating element (23) is situated in or adjacent to one or more of the reprocessing chamber walls (1a, 1b, 1c), the heater (22) is situated in the sump (71),
- heater (24) is situated inside buffer tank (3), the heater (21) is situated in or around the manifold (20) and/or any fluid line on the supply or discharge side of any process (2a) and or irrigation pump (2b).

4. The reprocessing apparatus according to claim 1 wherein the ultrasonic transducer (50) being in the form but not limited to at least one ultrasonic transducer attached to the outside of any of the chamber walls (1a, 1b, 1c) and/or doors and/or lids and/or at least one submersible transducer and/or bank or array of transducers.

5. A method of reprocessing a load in a reprocessing apparatus, where said load contains non-cannulated, non-hollow equipment with holes, crevices, hinges, joints, linkages (6a) and cannulated, hollow equipment (63b) which additionally contains internal channels and/or holes which depth is greater than the width including but not limited to medical, dental, laboratory, mortuary or veterinary instruments or equipment, said method comprising of the following steps:

initial rinsing comprising of delivering fresh water at a temperature below 45° C. through fluid distribution devices (61a and 61b) that deliver said water on the external and internal surfaces of the load as well as internal surfaces of a reprocessing chamber and additionally directly into the load (63b) though connecting lines (67a) for a predefined amount of time whilst draining contaminated fluid from the sump (71) through a drainage system, chemical washing without ultrasonication comprising of deactivating the drainage system and whilst delivering process fluid from the buffer tank (3) into the reprocessing chamber (1) through process and/or irrigation pump (2a, 2b) and fluid distribution devices (61a, 61b) and/or internal connection lines (67a, 67b), delivering predefined amount of process chemical together with fresh water into the buffer tank (3) to achieve desired concentration of the process chemical in the process fluid (80) that fills reprocessing chamber (1) and the reprocessing chamber (1) filling where said chamber fills up with process fluid (80) such that the load (63a) and/or load (63b) is at least partially submerged in the process fluid and simultaneously adjusting fluid temperature in the reprocessing chamber (1) to a desired level, ultrasonic cleaning comprising of disengaging the process pump (2 a), engaging at least one ultrasonic transducer (50)

at a frequency between 18 kHz and 10 MHz and power density of above 5 W per litre that create ultrasonic waves in the process fluid (80) contained in the reprocessing chamber (1) and remove contamination from surfaces of submerged within said fluid load (63a) and/or load (63b) whilst maintaining desired temperature of the process fluid (80) in the reprocessing chamber (1), continuing ultrasonic cleaning in the reprocessing chamber (1) delivering predefined amount of process chemical into the buffer tank (3) to achieve desired concentration of process chemistry in the process fluid (81) where said concentration is the same or above 5% higher or lower from one present in the process fluid (80) in the reprocessing chamber (1), alternatively to using different concentration of same chemical using different formulation of process chemical dedicated to internal cleaning of cannulated load (63 b) and pumping process fluid from buffer tank (3) through irrigation pump (2b) into dedicated fluid distribution devices (61b) and directly into the instruments (63b) through internal connection lines (67a, 67b), removing excess process fluid (80) from the reprocessing chamber (1), engaging the drainage system-reprocessing chamber draining—and the process pump (2a) and whilst continuing pumping the process fluid (81) from the buffer tank (3) and stopping delivery of the process chemistry to said tank and continuing supplying it with fresh water and thus removing said chemical from the buffer tank (3) whilst rinsing chemical residue from the reprocessing chamber (1) by delivering fresh water without chemicals from the buffer tank (3) to the fluid distribution devices (61a, 61b) and through internal connection lines (67a) directly to the load (63b) whilst allowing for process fluid (80) containing dissolved contamination and chemical residue to gradually drain out of the reprocessing chamber (1), further comprising of an optional disinfection step that is executed within one continuous washing and disinfecting cycle comprising deactivating the drainage system, delivering fresh water, preferably processed or purified and in case of chemical disinfection delivering required amount of disinfecting chemical into the buffer tank (3) and delivering such prepared fresh process fluid (81) into the reprocessing chamber (1) and allowing said chamber to fill to a desired minimum level being minimum head of water for pumps (2a) and/or pump (2b) to operate without cavitation during recirculation, simultaneously a recirculation loop through a valve (8a) and disengagement of the buffer tank (3) supply by closing a valve (8b) whilst continuing to recirculate the process fluid continuously from the sump (71) through the process (2a) and irrigation pumps (2b)

back to the reprocessing chamber (1) through fluid distribution devices (61a, 61b) and one or more connecting lines (67a, 67b), gradually elevating a process fluid temperature by the heater (21) and/or a reprocessing chamber wall heater (23) to at least 60° C., for thermal disinfection or at least 20° C. for chemical disinfection and while continually recirculating a disinfecting fluid maintaining such created environment for predefined amount of time until all exposed surfaces of the load (63a, 63b), instrument carrier/baskets (64a, 64b) and internal reprocessing chamber (1) walls receive sufficient disinfection dose, deactivating pumps (2a, 2b) and heating followed by activating the drainage system and discharging all remaining process fluid (80) out of the reprocessing chamber (1), wherein during filling the reprocessing chamber (1) the fresh water is mixed with process chemicals externally to said chamber in the buffer tank (3) and delivered to said chamber at predefined concentration through the fluid distribution devices (61a, 61b) and through the internal connecting lines (67a, 67b) while simultaneously washing the load (63a, 63b) internally and externally and washing the internal walls of the reprocessing chamber (1), during ultrasonic cleaning while the load (63a, 63b) is at least partially submerged in the process fluid (80), preparing a fresh process fluid (81) in the buffer tank (3) where said fluid contains at the same or at least 5% higher or lower concentration or a different type of the process chemical than one present in the reprocessing chamber (1) and pumping said fresh fluid through at least one irrigation pump (2b) through the dedicated fluid distribution devices (61b) and the internal connecting lines (67a, 67b) into internal elements of the load (63b)

periodically with a set duty cycle of 10% to 100% based on 10 s to 10 min time intervals whilst the load (63a, 63b) is being submerged in the process fluid (80) that distributes ultrasonic waves within its volume and simultaneously, removing an excess of process fluid (80) from the reprocessing chamber (1), additionally by the load (63*a* and 63*b*) being actively reprocessed-cleaned or disinfected-throughout the entire duration of the cycle such that there is no idle time greater than 1 min between subsequent parts of the process as the reprocessing fluid (81) is continually delivered into and drained from the reprocessing chamber (1) and the load (63*a*, 63*b*) is continually internally and/or externally reprocessed without the need to wait for water to fill in and/or drain from the reprocessing chamber (1), where transition between initial rinsing, chemical washing without ultrasonics, reprocessing chamber filling and draining and chemical residue rinsing happen whilst fresh process fluid is continually delivered into the reprocessing chamber through one or more fluid distribution devices (61*a*, 61*b*) and/or direct connection lines (67*a*, 67*b*), and further by ability of changing the fluid supply to process pump (2*a*) and irrigation pump (2*b*) between the fresh process fluid (81) from the buffer tank (3) and the used process fluid (80) from the sump (71) through the recirculation loop while continually supplying the process fluid (81, 80) to the fluid distribution devices (61*a*, 61*b*) and the internal connection lines (67*a*, 67*b*).

6. The method according claim 5 wherein further draining the reprocessing fluid (80, 81) from the reprocessing chamber (1) and optionally drying said load.

7. The method according to claim 5 wherein while the process pump (2*a*) and at least one irrigation pump (2*b*) are supplied from the buffer tank (3), washing process starts without having a minimum amount of the process fluid (81, 80) in the sump (71) and said pumps may continue washing with process chemicals or rinsing with the fresh hot, cold, processed and/or purified water while the reprocessing fluid (81, 80) is being drained from the reprocessing chamber (1).

8. The method according to claim 5 wherein the fluid is being pumped to the fluid distribution devices (61*a*, 61*b*) and connection lines (67*a*) from one or more buffer tanks, where temperature of said fluid is adjusted by mixing hot, cold, processed and/or purified water or by an internal (24) or external heater.

9. The method according to claim 5 wherein introducing one or more chemicals into each buffer tank (3) or directly into the reprocessing chamber (1).

* * * * *